United States Patent [19]

Burton

[11] 4,455,303

[45] Jun. 19, 1984

[54] RENIN INHIBITORS

[75] Inventor: James Burton, Amesbury, Mass.

[73] Assignee: The General Hospital Corporation, Boston, Mass.

[21] Appl. No.: 497,707

[22] Filed: May 24, 1983

[51] Int. Cl.³ ............... A61K 37/00; C07C 103/52
[52] U.S. Cl. .............................. 424/177; 260/112.5 R
[58] Field of Search .................. 260/112.5 R; 424/177

[56] References Cited

U.S. PATENT DOCUMENTS 4,224,316 9/1980 Momany ................. 260/112.5 R
4,228,158 10/1980 Momany ................. 260/112.5 R Primary Examiner—Delbert R. Phillips
Attorney, Agent, or Firm—Saidman, Sterne & Kessler

[57] ABSTRACT

A pentapeptide of the formula:

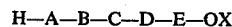

wherein
A, B, D are the same or different amino acid residues selected from the group consisting of Phe, Phe(4-Cl), Phe(4-F), Phe(4-Br), Phe(OMe), Tyr, Phe (4-I) and Tyr (ortho-Me);
C is Val, threo-α-amino-3-chlorobutyric acid, or Thr;
E is lysine or arginine;
X is $NH_2$, NHR, wherein R is $C_1$–$C_4$ alkyl, OH, $OR^1$, wherein $R^1$ is $C_1$–$C_4$ alkyl, or OM, where M is a physiologically acceptable cation or addition salts of said pentapeptide, is useful as a renin inhibitor.

8 Claims, No Drawings

RENIN INHIBITORS

BACKGROUND OF THE INVENTION

1. Field of the Invention

The present invention relates to renin inhibitors, more particularly to pentapeptide substrate analogues of renin, and their use in the treatment of hypertension.

2. Description of the Prior Art

Renin is an acid protease which cleaves the circulating protein angiotensinogen to yield the decapeptide angiotensin I. This is converted into angiotensin II, which controls blood pressure in animals by mechanisms which include constriction of the vascular smooth muscle and regulation of salt and water balance. Angiotensin II is known to be involved in renovascular hypertension, and a role is postulated for this substance in the etiology of essential hypertension. A clinically useful renin inhibitor would have therapeutic relevance for the treatment of these conditions.

There are four classes of compounds which specifically prevent the production of angiotensin by renin. First, antibodies which bind renin can specifically inhibit the enzyme. The use of such antibodies has been reported to lower blood pressure in primates.

The second approach is to use one of the pepstatins, which are low molecular weight protease inhibitors obtained from the culture medium of Streptomyces. (See for example Gross et al, Science 175: 656 (1971), Miller et al, Biochem. Pharmacol. 21, 2941–2944 (1972), and Aoyagi et al, J. Antibiot. 25: 689–694 (1972)). More tractable analogues of pepstatin with greater solubility have been reported (Eid et al, Biochem. J. 197(2): 465–471, (1981), Miyazaki et al, Japan J. Pharmacol. 28: 171–174 (1978)). The data indicate reversal of renin dependent hypertension in the rat and dog with these analogues.

A third approach involves the use of small peptides based on the sequence of angiotensinogen (Kokubo et al, Biochem. Pharm. 22: 3217–3223 (1973)). Poulsen et al (Biochemistry 12: 3877–3882 (1973)) showed that the inhibitory constant for a representative member of the series was about three orders of magnitude greater than for longer inhibitors (such as, e.g. those developed by Burton et al (Proc. Nat. Acad. Sci. USA, 77: 5476–5479 (1980)). Other short inhibitors in which the alpha amino group is replaced by a hydroxyl group have been reported.

Burton et al (Proc. Nat. Acad. Sci., supra) have reported the use of longer substrate analogues for the inhibition of renin in primates. The Renin Inhibitory Peptide (RIP, U.S. Pat. No. 4,269,827, herein fully incorporated by reference), is effective in inhibiting renin in primates. Paiva et al (Oliveira et al, Proc. 7th Amer. Pept. Symp., Pierce Chem Co., Rockford, Ill. 1982, 435–438) have prepared constrained analogues of RIP which are moderately active in vitro but have not been tested in vivo.

Research by Skeggs et al (J. Exp. Med. 128: 13–34 (1968)) indicates that short substrates do not effectively inhibit renin. Poulsen et al (Biochem. 12: 3877–3882 (1973)), for example, have reported that the tetrapeptide Leu-Leu-Val-TyrH$_2$ has an inhibitory constant (K$_I$) of 1020 micromolar at pH 7.4. Johnson (J. Med. Chem. 23: 666–669 (1980)) found a similar K$_I$ for the tetrapeptide Leu-Leu-Val-Phe-OCH$_3$ at pH 7.0. These peptides are about 0.2% as effective as RIP in preventing the formation of angiotensin I by renin.

One particular modification of interest to those of skill in this art would be to develop peptides which are orally active. Modification of RIP, for example, to yield an orally active renin inhibitor would require both a reduction in the size of the inhibitor and an increase in lipophilicity. In addition, an acceptable peptide must be made resistant to digestion by proteolytic enzymes of the gastrointestinal tract. These objectives must be accomplished without markedly diminishing inhibitory potency.

A need therefore continues to exist for inhibitors of renin useful for treatment of hypertension, especially renin-dependent hypertension.

SUMMARY OF THE INVENTION

It is therefore an object of the invention to provide renin inhibitors.

Another object of the invention is to provide pentapeptide renin inhibitors with biological activity useful in the treatment of hypertension.

It is another object of the invention to provide pharmacological compositions comprising renin inhibitors.

Still another object of the invention is to provide a method of decreasing hypertension in animals including humans.

These and other objects of the invention as will hereinafter become more readily apparent have been attained by providing:

A pentapeptide of the formula:

wherein

A, B, D are the same or different amino acid residues selected from the group consisting of: Phe, Phe (4-Cl), Tyr, Phe (4-I) and Tyr (ortho-Me)

C is Val, Thr or threo-$\beta$-amino-3-chlorobutyric acid;

E is lysine or arginine;

X is NH$_2$, OH, or OM, where M is a physiologically acceptable cation;

or addition salts of said pentapeptide.

The objects of the invention have also been attained by providing pharmacological compositions comprising the aforementioned pentapeptide, and methods of treating hypertension in animals including humans comprising using said pentapeptide.

BRIEF DESCRIPTION OF THE PREFERRED EMBODIMENTS

The compounds of the present invention comprise those having the formula:

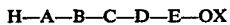  (1)

In this formula, A, B, C, D and E are individual amino acid residues. A, B and D may be the same or different and are selected from the group consisting of phenylalanine (Phe), 4-chlorophenylalanine (Phe(4-Cl)), 4-fluorophenylalanine (Phe(4-F)), 4-bromophenylalanine (Phe(4-Br)), methoxyphenylalanine (Phe(OMe)), tyrosine (Tyr), 4-iodo-phenylalanine (Phe(4-I)) and ortho-methyl tyrosine (Tyr(ortho-Me)). C is valine (Val), threo-$\alpha$-3-chlorobutyric acid (Bca) or threonine (Thr). E is lysine (Lys) or arginine (Arg). X is NH$_2$ (in which case the pentapeptide is in the form of the C-amide), NHR, wherein R is C$_1$–C$_4$ alkyl, OH (in which case the pentapeptide is in the form of the free acid), $OR^1$, wherein $R^1$ is $C_1$–$C_4$ alkyl, or OM (in which case the pentapeptide is in the form of the C-terminus salt), where M is a cation. Useful cations are alkaline or alkaline earth metallic cations (e.g. Na, K, Li, Ca, etc.) or amine cations (e.g. tetralkyl ammonium, trialkyl ammonium, where alkyl can be $C_1$–$C_{12}$).

The pentapeptides may be in the form of the free amines (on the N-terminus) or acid addition salts thereof. Common acid addition salts are hydrohalic acid salts, for example HBr, HF, or, more preferably, HCl.

Preferred are those pentapeptides having a C-terminal amide. Also preferred are those having a Lys as the C-terminal amino acid residue-5.

Representative pentapeptides of the present invention are:
$H_2N$-Phe-Phe-Val-Tyr-Lys-$CONH_2$
$H_2N$-Tyr-Phe-Val-Tyr-Lys-$CONH_2$
$H_2N$-Phe(4Cl)-Phe-Val-Tyr-Lys-$CONH_2$
$H_2N$-Phe-Tyr-Val-Tyr-Lys-$CONH_2$
$H_2N$-Phe-Phe(4Cl)-Val-Tyr-Lys-$CONH_2$
$H_2N$-Phe-Tyr(Me)-Val-Tyr-Lys-$CONH_2$
$H_2N$-Phe-Phe(4-I)-Val-Tyr-Lys-$CONH_2$
$H_2N$-Phe-Phe-Thr-Tyr-Lys-$CONH_2$
$H_2N$-Phe-Phe-Bca-Tyr-Lys-$CONH_2$
$H_2N$-Phe-Phe-Val-Phe-Lys-$CONH_2$
$H_2N$-Phe-Phe-Val-Phe(4Cl)-Lys-$CONH_2$ The most preferred pentapeptide of this invention is $H_2N$-Phe-Phe(4Cl)-Val-Tyr-Lys-$CONH_2$, and its acid addition salts.

The peptides can be synthesized by the well known solid phase peptide synthesis (Merrifield, R. B., J. Am. Chem. Soc. 85: 2149–2154 (1963), and Burton, Biochem. 14: 3892–3898 (1975)), using a benzhydrylamine support containing 0.44 mMol amine/g polymer. On completion of chemical synthesis, the peptides can be deprotected and cleaved from the polymer by treatment with liquid HF-10% anisole for about 1 hour at 0° C. After evaporation of the reagents, the peptides are extracted from the polymer with 1% acetic acid solution which is then lyophilized to yield the crude material. This can normally be purified by such techniques as gel filtration on Sephadex G-15 ® using 5% acetic acid as a solvent. Lyophilization of the appropriate fractions of the column eluate yield the homogeneous pentapeptide amides, which are characterized by amino acid analysis, thin layer chromatography, high performance chromatography, ultraviolet absorption spectroscopy, molar rotation, solubility, and renin inhibitory potential.

The technique of synthesis and isolation is fully described in the aforementioned references, as well as in U.S. Pat. No. 4,269,827 which is incorporated by reference. It is to be noted that during the synthesis, lysines are preferably blocked by 2-chlorobenzyloxy carbonyl, tyrosines are preferably blocked with 2,6-dichlorobenzyl and terminal amino groups are preferably blocked with the t-boc group. Other protective blocking groups are well-known and can be used in the present invention.

The assay for testing the inhibitory activities of the pentapeptides on renin is described in Burton, J. et al, Biochem. 14: 3892–3898 (1975), which is herein incorporated by reference.

The pentapeptides of the present invention are useful in the inhibition of renin, and thus in the treatment of renin-dependent hypertension. The modes and manner of administration are similar to those for RIP described in U.S. Pat. No. 4,269,827.

Of particular interest is the fact that the peptides of the present invention are short chained, and can potentially be used as orally active peptides. This is supported by the observation that the preferred peptide ($H_2N$-Phe-Phe(4Cl)-Val-Tyr-Lys-$CONH_2$) has been shown to be transported across the gut in an in vitro experiment. Thus, when this radiolabeled pentapeptide was added to one side of an isolated gut section, label could be detected and measured as appearing on the other side, indicating that the pentapeptide was transported across the gut.

A standard method of administration to animals would be by injection. Oral administration could be provided in an oral preparation given either through a nasogastric tube to bypass stomach acid, or in well known formulations in pills which render the peptide acid or pharmaceutically acceptable derivative thereof resistant to gastric acid.

The pentapeptide is placed in a known pharmaceutically acceptable vehicle, the nature of which varies depending on the mode of administration of the pentapeptide.

The pentapeptides can be provided to animals including domestic animals suffering hypertension, and humans. The dosage and mode of administration will depend on the seriousness of the hypertension, the age, sex and physical condition of the patient, concurrent administration of other drugs, counter indications and the like. Generally, a dosage of between 1 and 50 gm per day, most preferably 5–25 gm per day for a normal adult would be sufficient.

Having now generally described this invention the same will be understood by reference to certain specific examples which are included herein for purposes of illustration only and are not intended to be limiting unless otherwise specified.

Example 1

The 11 pentapeptides shown in Table I were synthesized by standard solid phase peptide synthesis as shown in the description following the table and the $IC_{50}$ (concentration at which inhibition is 50%) value on human renin in the assay of Burton et al, supra, was determined for each sample. Results are shown in Table I.

TABLE I

| Sample No. | | $IC_{50}$ μm |
|---|---|---|
| RI-77 | $H_2N$—Phe—Phe—Val—Tyr—Lys—$CONH_2$ | 80 |
| RI-79 | $H_2N$—Tyr—Phe—Val—Tyr—Lys—$CONH_2$ | 140 |
| RI-78 | $H_2N$—Phe(4Cl)—Phe—Val—Tyr—Lys—$CONH_2$ | 70 |
| RI-81 | $H_2N$—Phe—Tyr—Val—Tyr—Lys—$CONH_2$ | 80 |
| RI-80 | $H_2N$—Phe—Phe(4Cl)—Val—Tyr—Lys—$CONH_2$ | 40 |
| RI-102 | $H_2N$—Phe—Tyr(Me)—Val—Tyr—Lys—$CONH_2$ | 190 |
| RI-103 | $H_2N$—Phe—Phe(4-I)—Val—Tyr—Lys—$CONH_2$ | 200 |
| RI-83 | $H_2N$—Phe—Phe—Thr—Tyr—Lys—$CONH_2$ | 3750 |
| RI-82 | $H_2N$—Phe—Phe—Bca—Tyr—Lys—$CONH_2$ | 1250 |
| RI-84 | $H_2N$—Phe—Phe—Val—Phe—Lys—$CONH_2$ | 750 |
| RI-85 | $H_2N$—Phe—Phe—Val—Phe(4Cl)—Lys—$CONH_2$ | 100* |

*Because of insolubility, it was impossible to define this value accurately.

Peptide Synthesis tert-Butyloxycarbonylamino acids were purchased from Peninsula Inc. (San Mateo, CA). Side chain protecting groups are: lysine, 2-chlorobenzyloxycarbonyl; tyrosine, 2-bromobenzyloxycarbonyl; and histidine, tosyl. Tritiated tert-butyloxycarbonyl-phenylalanine, -valine, and -proline were prepared by reaction of the labeled amino acid (New England Nuclear, Boston, MA) which had been diluted to the desired specific activity with unlabeled amino acid (Eastman, Rochester NY), with $(Bu^tO)_2CO$* (Tridom, Hauppage, NY). The $Bu^tOCO$ derivatives of L-4-chloro-phenylalanine, L-4-iodophenylalanine, O-methyl-L-tyrosine (Serva, Garden City Park, NY) and threo-3-chloro-L-2-aminobutyric acid (CalBiochem, San Diego, CA) were prepared using $(Bu^tO)_2CO$ as described for preparation of the labeled amino acid derivatives. The protected amino acid derivatives were homogeneous on thin layer chromatography (tlc).

*Nomenclature used for the description of peptides is given in J. Biol. Chem. 247 977-983, 1972.

$Et_3N$ was purchased from Pierce Chemical Co. (Rockford IL), $CF_3COOH$ was obtained from Aldrich Chemical Co. (Milwaukee, WI) and dicyclohexylcarbodiimide was obtained from Schwartz Mann (Orangeburg, NY). BOP (Castro, et al., 1976) was purchased from SST Inc. (Clifton, NJ). $CH_2Cl_2$ was distilled from $CaH_2$ (Perrin, D. D., et al., 1966, "Purification of Laboratory Organic Chemicals", Oxford, Pergamon Press, p. 132). The support used for solid phase synthesis was either LS-601 Merrifield Resin containing 0.75 mM Cl $g^{-1}$ (Laboratory Systems Inc., San Mateo, CA) or benzhydrylamine resin containing 0.40 mM -$NH_2$ $g^{-1}$ (Peninsula Inc., San Mateo, CA). 1-Octanol was distilled at reduced pressure (bp 90°). Other reagents were of analytical grade.

Synthetic reactions were performed in 50 or 60 mL polypropylene syringes fitted with a polyethylene frit (70μ porosity, BoLab, Derry, NH) using apparatus and techniques previously described (Burton, J. et al, 1975, *Biochemistry*, 14, 3892-3898; Merrifield, R. B., 1964, *J. Am. Chem. Soc.*, 86, 304-305). Completeness of coupling was judged with the ninhydrin test (Kaiser, E. et al (1970) *Anal. Biochem.* 34, 595-598). The C-terminal amino acid was attached using procedures described by Stewart, J. M. and Young, J. D. (1969), "Solid Phase Peptide Synthesis," Freeman, San Francisco, Calif., or Pietta, P. G. and Marshall, G. R., (1970), *Chem. Comm.*, 650.

A protocol for preparation, cleavage, and extraction of the synthetic peptide was generated using the computer program MACBETH (Burton, J., Rosenthal, S. and Rosenthal, J., In Preparation).

Amino acid analyses were performed with a Durrum D-500 analyzer. The best fit of data to the theoretical composition was made using the computer program PEPTALK (Burton, J., Topper, R., Rosenthal, J., and Rosenthal, S., In Preparation). Minimum variance of the computed number of each amino acid residue from the theoretical value is reported with the analyses as the variance.

U-v spectra were obtained on an HP 8450A spectrophotometer equipped with an HP 7225 plotter (Hewlett Packard, Inc., Palo Alto, CA). Spectra were normalized using the equation $(A_x - A_{310}/A_{max} - A_{310})$. Normalized spectra from different peptides could be superimposed for comparison.

High pressure liquid chromatography (hplc) was done with a 410 system (Beckman Instruments Inc., Palo Alto, CA) eluted through a 178.32 flow cell (Hellma, Jamaica, NY) in the HP 8450 spectrophotometer. The wavelength chromatography program developed by J. James (HP UV/VIS Note 82/9) was used to construct and analyze elution profiles. Modification of the program allowed collection of the hplc effluent whose u-v absorbance exceeded a preset value (Quinn, T., personal communication). Hplc purifications were effected on a semipreparative Beckman ODS column (10×250 mm). Two systems were employed for characterization. The peptide was chromatographed either on an ODS column (4×250 mm) eluted with 30% (v/v) $CH_3CN$—0.2% $CF_3COOH$, the retention time measured, and reported as k. Alternatively, the semipreparative ODS column (10×250 mm) was eluted with a 10–90% gradient of $CH_3CN$ over 1800 sec. and elution time of the peptide reported.

Other apparatus used has been described previously (Burton, J. et al, (1975), Biochemistry, 14, 3892-3898).

Distribution coefficients (P) were measured by dissolving the peptide in 0.01 M phosphate buffer (pH 7.40) in 0.15 M saline (PBS), carefully re-adjusting the pH to 7.40, and then vortexing 0.50 mL of this solution with 0.50 mL 1-octanol for 1 minute. The emulsion was centrifuged for 5 min. in a Microfuge (Beckman, Palo Alto, CA) and the phases separated and counted along with blanks and standards. The computer program P-VALUE (K. Takaori, personal communication) was used to calculate P values from the data.

Prolylhistidylprolylphenylalanylhistidylphenylalanyl-phenylalanylvalyltyrosyllysine, R-68, RIP RI-68 was synthesized with a labeled prolyl residue at the N-terminal position. BOP (Castro, B. et al, 1975) was used for formation of the peptide bonds. Boc-His(-Tos).DCHA was not desalted but incorporated with a five rather than ten-fold excess of $Et_3N$ in the reaction mixture. The product was purified by chromatography on Sephadex G-25 and Biogel P2 as described previously (Cody, R. et al, (1980) Biochem. Biophys. Res. Comm., 97, 230-235). Physical properties of the peptide match those reported.

Lys, 0.90; Tyr, 0.81; Val, 0.93; Phe, 3.05; His, 2.00; Pro, 2.08; variance, 0.011; M $_{578\ nm}$, +1300° (1 M $CH_3COOH$); 0.157 Ci Mol$^{-1}$; P, −1.12, $IC_{50}$, 0.02.

Phenylalanylphenylalanylvalyltyrosyllysine-amide, R-77

The C-terminal lysyl residue was attached to the benzhydrylamine polymer using DCC to yield a negative ninhydrin reaction. 170 Mol lysine were incorporated/g polymer Synthesis of RI-77 was begun with 0.88 g (150 Mol) of the amino acyl-polymer. The phenylalanine in the 2-position was incorporated as the tritiated derivative. On completion of the synthesis, the peptidyl polymer was deprotected, washed with $CH_2Cl_2$; EtOH and dried over $P_2O_5$ to yield 1.07 g peptidyl polymer. The polymer was treated with 10 mL HF containing 10% (v/v) anisole for 1 hr at 0°. On completion of the cleavage, HF and anisole were evaporated at high vacuum and the reaction mixture transferred to a coarse Hirsch funnel (Porosity A, Ace, Vineland, NJ) with 50 mL cold ethyl acetate. The polymer was then sequentially extracted with 100 mL 1%, 5%, 10%, and 25% acetic acid solutions and each extract counted. Radioactivity (100%) was found in the 1% extract which was lyophilized to yield 240 mg of a white powder (100%). 50 mg of the crude extract was dissolved in 3 mL 5% acetic acid solution and chromatographed in the same solvent on Sephadex G-15 (1.0×115 cm). 2.0 mL fractions were collected and the u-v absorbance (280 nM) and radioactivity (Ci $L^{-1}$) measured and plotted using the computer program CHROMO (T. Quinn, personal communication). Fractions having a constant ratio of absorbance to specific activity were pooled and lyophilized to yield 22.8 mg RI-77 (67%).

Phe, 2.10; Val, 0.90; Tyr, 0.96; Lys, 0.91; variance, 0.71 Ci Mol$^{-1}$. $\epsilon$280 nM, 1315; M $_{578\ nM}$, +4593°; $R_F$ (T3) front, (T4) 0.29, (T6) 0.65. hplc, homogeneous; k, 0.57; P, −0.43; IC$_{50}$, 1.02 mM.

4-chlorophenylalanylphenylalanylvalyltyrosyllysine-amide, RI-78

0.88 g of the solid support containing 150 Mol lysine prepared during the synthesis of RI-77 was used for the synthesis of RI-78. The phenylalanine residue at position-3 was incorporated as the tritiated derivative. After synthesis and deprotection, the peptidyl polymer (1.11 g) was cleaved and extracted to yield 0.24 g crude peptide (100%). 40 mg of the crude extract was purified to homogeneity by chromatography on Sephadex G-15 as described and fractions eluting between 68–78 mL were pooled and lyophilized to yield homogeneous RI-78 (58%).

Lys, 0.97; Tyr, 1.05; Val, 1.00; Phe, 0.98, Phe(4Cl)*, not done; variance, 0.001. 0.80 Ci Mol$^{-1}$, $\epsilon$280 nM, 2511, M $_{578\ nM}$, +1569°; $R_F$ (T3) front, (T4) 0.34, (T6) 0.66; k, 1.82; P, 0.069; IC$_{50}$, 0.07 mM.
*Not included in the averaging process.

Tyrosylphenylalanylvalyltyrosyllysine-amide, RI-79

0.88 g of the solid support containing 150 Mol lysine was used for preparation of RI-79. The phenylalanine residue at position-3 was incorporated as the tritiated derivative. Yield of the peptidyl polymer is 1.11 g. Cleavage and extraction yielded 0.230 g crude peptide (100%). 50 mg of the crude extract was chromatographed on Sephadex G-15 and fractions eluting between 70–86 mL pooled and lyophilized to yield homogeneous RI-79 (44%).

Lys, 1.03; Tyr, 1.99; Val, 0.92; Phe, 1.06; variance, 0.003; 0.94 Ci Mol$^{-1}$, $\epsilon$280 nM, 3469; M$_{579\ nM}$, +311°; $R_F$ (T3) front, (T4) 0.28; (T6) 0.62; k, 0.42; P, −0.56; IC$_{50}$, 0.050 mM.

Phenylalanyl-4-chlorophenylalanylvalyltyrosyllysineamide, RI-80

0.88 g of the solid support containing 150 Mol lysine was used for preparation of RI-80. The N-terminal phenylalanyl residue was incorporated as the tritiated derivative. Yield of the deprotected peptidyl polymer was 1.01 g (90%). Cleavage of the polymer with HF-10% anisole yielded 0.210 g of a white powder. 37 mg of the crude extract was dissolved in 5% acetic acid solution and chromatographed on Sephadex G-15. Fractions eluting between 76–84 mL were pooled and lyophilized to yield homogeneous RI-80 (49%).

Lys, 1.00; Tyr, 0.92; Val, 0.96; Phe (4Cl)*, not done; Phe, 1.10; variance, 0.006; 0.49 Ci Mol$^{-1}$, $\epsilon$280 nM, 1255; M $_{579\ nM}$, +7485°, $R_F$ (T3) front; (T4) 0.34; (T6) 0.67; k, 1.70; P, 0.045; IC$_{50}$, 0.64 mM.

Phenylalanyltyrosylvalyltyrosyllysine-amide, RI-81

0.88 g of the solid support containing 150 Mol lysine was used for preparation of RI-81. The N-terminal phenylalanine residue was incorporated as the tritiated derivative. Yield of the deprotected peptidyl polymer was 1.14 g (98%). Cleavage with HF-10% anisole yielded 0.23 g of a white powder. 37.5 mg was chromatographed on Sephadex G-15 and fractions eluting between 62–72 mL pooled and lyophilized to yield homogeneous RI-81 (62%).

Lys, 1.02; Tyr, 2.00; Val, 0.99; Phe, 1.01, variance, 0.000; 0.59 Ci Mol$^{-1}$. $\epsilon$280 nM, 2924; M$_{579\ nM}$, +1073°; $R_F$(T3) front, T4, 0.28; T6, 0.62; k, 0.30; P, 0.47; IC$_{50}$, 0.15 mM.

Phenylalanylphenylalanyl-threo-3-chloro-L-2-aminobutyryltyrosyllysine amide, RI-82

0.88 g of the solid support containing 150 Mol lysine was used for preparation of RI-82. The phenylalanyl residue at position 2 was incorporated as the tritiated derivative. Yield of the deprotected peptidyl polymer was 1.13 g (100%). Cleavage with 11 mL HF-10% anisole, extraction, and lyophilization yielded 0.240 g crude peptide. 46.8 mg of this was dissolved in 2.5 mL acetic acid solution and chromatographed on Sephadex G-15. Fractions eluting between 60–70 mL were lyophilized to yield homogeneous RI-82 (55%).

Lys, 1.00; Tyr, 0.93; Cba*, not done; Phe, 2.03, variance, 0.003; 0.49 Ci Mol$^{-1}$; $\epsilon$280 nM, 1237; M $_{579\ nM}$, +696°; $R_F$ : T3, front; T4, 0.31; T6, 0.65; k, 1.36; P, −0.59; IC$_{50}$, 2.45 mM.

Phenylalanylphenylalanylthreonyltyrosyllysine-amide, RI-83

0.88 g of the solid support containing 150 Mol lysine was used for preparation of RI-83. The phenylalanyl residue at position 2 was incorporated as the tritiated derivative. Yield of the deprotected peptidyl polymer was 1.13 g (100%). Cleavage of this with 11 mL HF-10% anisole, extraction, and lyophilization yielded 0.20 g of crude peptide. 41.0 mg of this was chromatographed on Sephadex G-15 and fractions eluting between 60–70 mL were pooled and lyophilized to yield the homogeneous RI-83 (56%).

Lys, 1.04; Tyr, 0.95; Thr, 0.94; Phe, 2.03, variance, 0.003. 0.49 Ci Mol$^{-1}$, $\epsilon$280 nM, 1349; M$_{579\ nM}$, +560°; $R_F$: T3, front; T4, 0.25; T6, 0.61; k, 0.57; P, −0.73.

Phenylalanylphenylalanylvalylphenylalanyllysine-amide, RI-84

0.88 g of the p-methylbenzhydrylamine polymer containing 208 Mol lysine (236 M lysine/g) was prepared for the synthesis of RI-84. The phenylalanyl residue at position-2 was incorporated as the tritiated derivative. Yield of the deprotected peptidyl polymer was 1.02 g (95%). Cleavage with 11 mL HF-10% anisole, extraction and lyophilization yielded 0.18 g white powder. 41.7 mg of this was dissolved in 2 mL 5% acetic acid solution and chromatographed on Sephadex G-15. Fractions eluting between 58–68 mL were pooled and lyophilized to yield homogeneous RI-84 (62%).

Lys, 0.98; Phe, 3.03; Val, 0.92; variance, 0.004; 0.54 Ci Mol$^{-1}$; $\epsilon$280 nM, 542; M $_{579\ nM}$, +994°; $R_F$: T3, front; T4, 0.31; T6, 0.71; k, 2.89; P, −0.072.

Phenylalanylphenylalanylvalyl-4-chlorophenylalanyllysine-amide, RI-85

0.88 g of the solid support containing 208 Mol lysine was used for preparation of RI-84. The phenylalanyl residue at position-2 was incorporated as the tritiated derivative. Yield of the deprotected peptidyl polymer was 1.07 g (99%). Cleavage of the polymer with 11 mL HF-10% anisole, extraction and lyophilization yielded 0.21 g crude material. 45.8 mg of the crude peptide was chromatographed on Sephadex G-15. Fractions eluting between 66–74 mL were pooled and lyophilized to yield the homogeneous RI-85 (56%).

Lys, 1.00; Phe(4Cl)*, not done; Val, 0.92; Phe, 2.03, variance, 0.004; 0.50 Ci Mol$^{-1}$; $\epsilon$280 nM, 119; M $_{578\,nM}$, +379°; R$_F$: T3, front; T4, 0.33; T6, 0.72; k, 6.07; P, 0.45; IC$_{50}$, 0.175 mM.

Phenylalanyl-O-methyltyrosylvalyltyrosyllysine-amide, RI-102

The solid phase synthesis of RI-102 was initiated with 0.99 g polymer containing 234 Mol lysine. The N-terminal phenylalanyl residue was incorporated as the tritiated derivative. On completion of the synthesis, the yield of the peptidyl resin was 1.32 g. Cleavage of this with 13 mL HF-10% anisole for 1.25 hrs at 0° followed by evaporation, extraction and lyophilization of the 1% acetic acid extract yielded 229 mg white powder. 25 mg of the powder was dissolved in 3 mL 5% acetic acid solution and chromatographed on Sephadex G-15. Fractions eluting between 62–74 mL were pooled and lyophilized to yield homogeneous RI-102 (91%).

Lys, 1.05; Tyr, 1.90, Val, 1.07, Tyr(Me), not done, Phe, 1.05; variance, 0.006; 0.25 Ci Mol$^{-1}$, $\epsilon$280 nM, 3186, M $_{578\,nM}$, +1066°; R$_F$: T3, 0.86; T4, 0.37; T6, 0.69. hplc, 1488 sec.; P, −0.724; IC$_{50}$, 0.86 mM.

Phenylalanyl-4-iodophenylalanylvalyltyrosyllysine-amide, RI-103

0.99 g polymer containing 234 M lysine was used for the synthesis of RI-103. The valyl residue was incorporated as the tritiated derivative. On completion of the synthesis yield of the peptidyl resin was 1.34 g. Cleavage with 13 mL HF-10% anisole for 1.25 hrs at 0° followed by evaporation, extraction and lyophilization of the 1% extract yielded 233 mg white powder. 25 mg of this was dissolved in 2.4 mL 5% acetic acid solution and chromatographed on Sephadex G-15. Fractions eluting between 50–70 mL were pooled and lyophilized to yield the homogeneous RI-103 (75%).

Lys, 1.06; Tyr, 0.96; Val, 0.98; Phe(41)*, not done; Phe, 1.02; variance, 0.003; 0.26 Ci Mol$^{-1}$; $\epsilon$280 nM, 2078; M $_{578\,nM}$, 414; R$_F$: T3, 0.88; T4, 0.45; T6, 0.68; P, +0.23: IC$_{50}$, 0.02.

Phenylalanylphenylalanylvalyltyrosyllysine, RI-108

1.76 g polymer containing 500 M lysine was used for the synthesis of RI-108. Boc-Lys(2Cl-Z) was esterified to the chloromethyl polymer using standard techniques described in Stewart, J. M., Young, J. D., (1969), "Solid Phase Peptide Synthesis", Freeman, San Francisco, Calif. The valyl residue was incorporated as the tritiated derivative. On completion of synthesis, yield of the peptidyl resin was 2.26 g. Cleavage with 25 mL HF-10% anisole, evaporation, and extraction yielded a crude product, on lyophilization. An amount of the crude material was dissolved in 5% acetic acid and chromatographed on Sephadex G-15 (2.5×115 cm). The fractions eluting between 553–585 mL were pooled and lyophilized to yield homogeneous RI-108 (40%).

Lys, 1.06; Tyr, 0.92; Val, 1.01; Phe, 2.00; variance, 0.003; 0.25 Ci Mol$^{-1}$; $\epsilon$280 nM, +3319°; M $_{578\,nM}$; R$_F$: T3, 0.94; T4, 0.32; T2, 0.32; hplc, 1500 sec.; P, 0.14.

Phenylalanylphenylalanylvalyltyrosyl-D-lysine-amide, RI-111

1.77 g benzhydrylamine polymer containing 500 M lysine were used for the synthesis of RI-111. The valyl residue was incorporated as the tritiated derivative. On completion of the synthesis, the weight of the peptidyl resin was 2.79 g. Cleavage with 25 mL HF-10% anisole, evaporation, and extraction yielded after lyophilization of the 1% extract, a white powder. An amount of the white powder was dissolved in 12 mL 5% acetic acid solution and chromatographed on Sephadex G-15 (2.5×115 cm). Fractions containing the desired pentapeptide were pooled and lyophilized to yield (40%) homogeneous RI-111.

Lys, 0.98; Tyr, 0.90; Val, 0.95; Phe, 2.03; variance, 0.002; 0.028 Ci Mol$^{-1}$; $\epsilon$280 nM, 1391; M $_{589\,nM}$, +; R$_F$: TD3, 0.71; T4, 0.33; T6, 0.63; hplc, sec.; P, −0.60.

In Vitro Testing

Angiotensin I standards and tetradecapeptide renin substrate (TDP) were obtained from Peninsula Laboratories Inc. (San Mateo, CA). Renin was a gift of Dr. E. Slater (1980). Angiotensin I concentration was determined by radioimmunoassay using a commercially available kit (Clinical Assays, Cambridge, MA).

For IC$_{50}$ determinations, TDP solutions having a concentration of 37.5 molar was prepared by dissolving TDP in 0.01 N HCl and diluting with 0.1 M Tris-0.1% lysozyme buffer (pH 7.40). Standard renin solution (V3) is diluted 4-fold with M Tris-lysozyme buffer (pH 7.40). Concentration of 5000, 2500, 1250, 500, and 250 molar of the renin inhibitor being tested are also prepared in the Tris-lysozyme buffer. For the uninhibited reaction Tris-lysozyme buffer alone is used in place of the inhibitor solution.

Reaction mixtures containing TDP solution (150 liters, 25 M), renin solution (50 liters, 20-fold diluted), and the inhibitor (50 liters, 50–1000 M) were incubated for 1 hr at 37°, diluted 1000-fold and assayed for angiotensin I.

Inhibition is determined by the following equation:

$$\% \text{ Inh.} = ((ng\, ANG\, I_{unhib} - ng\, ANG\, I_{inh})/ng\, ANG\, I_{unhib}) \times 100$$

IC50 is determined by plotting Percent inhibition (% Inh.) against the inhibitor concentration and interpolating to determine the molarity of inhibitor at which 50% inhibition is observed.

Cross-reactivity of TDP with ANG I is less than 0.05%. Addition of 8-hydroxyquinoline or Trasylol to the reaction mixture does not affect the rate of generation of ANG I.

In Vivo Testing

The animal model of acute renovascular hypertension is prepared by surgically implanting an inflatable cuff about the aorta above the left kidney of an adult *Macaca fascicularis* as descirbed by Cody, R. J. et al (1980) *Hypertension*. The right kidney is subsequently removed and catheters implanted in the right iliac vein and artery. Two arterial catheters lead from above and below the constricting cuff to strain gauges permit blood pressure to be measured both above and below the cuff.

Inflation of the cuff creates a measurable amount of ischemia to the remaining kidney and renin dependent hypertension develops in about one hour.

The results of the injection of (RI-78) on the blood pressure and plasma renin level of one monkey are summarized below. The converting enzyme inhibitor teprotide (Ondetti et al, 19) is used as a control.

| Cuff Status | Time* (minutes) | Injection | Blood Pressure (mm Hg) | Plasma Renin Activity |
|---|---|---|---|---|
| Deflated | −175 | — | 95 | 9.6 |
| Inflated | −55 | — | 110 | 21.5 |
| Inflated | −15 | 1.0 mL D5W | 113 | — |
| Inflated | 0 | 0.5 mg RI-78 | 113 | — |
| | 10 | 2.5 mg RI-78 | 65 | — |
| Inflated | 12 | — | | — |
| Inflated | 14 | — | | — |
| Inflated | 16 | — | | — |
| Inflated | 20 | — | | — |
| Inflated | 25 | — | 111 | — |
| Inflated | 30 | — | | 28.5 |
| Inflated | 145 | Teprotide | 76 | 37+ |

Having now fully described this invention it will be appreciated by those of skill in the art that same can be practiced within a wide and equivalent range of compositions, modes of administration, therapeutic treatments, and the like, without effecting the spirit or scope of the invention or any embodiment thereof.

What is claimed as new and intended to be covered by Letters Patent of the United States is:

1. A pentapeptide of the formula:

H—A—B—C—D—E—OX wherein
   A, B, D are the same or different amino acids residues selected from the group consisting of Phe, Phe(4-Cl), Phe(4-F), Phe(4-Br), Phe(OMe), Tyr, Phe(4-I), and Tyr (ortho-Me);
   C is Val, Thr or threo-α-amino-3-chlorobutyric acid;
   E is lysine or arginine;
   X is $NH_2$, NHR, wherein R is $C_1$–$C_4$ alkyl, OH, OR′, wherein $R^1$ is $C_1$–$C_4$ alkyl, or OM; where M is a physiologically acceptable cation;
   or addition salts of said pentapeptide.

2. The pentapeptide of formula 1 wherein E is lysine.

3. The pentapeptide of formula 1 wherein A is phenylalanine.

4. The pentapeptide of claim 1 which is $H_2N$-Phe-Phe(4Cl)-Val-Tyr-Lys-$CONH_2$.

5. A composition comprising a renin inhibitory effective amount of the pentapeptide of claims 1 or 4, together with a pharmacologically inert carrier.

6. The composition of claim 5, in unitary dosage form.

7. A method of decreasing hypertension in animals which comprises administering to said animals a hypertension decreasing amount of the pentapeptide of any of claims 1 or 4.

8. The method of claim 7 wherein said pentapeptide is administered orally.

* * * * *